US010386399B2

United States Patent
Chen

(10) Patent No.: US 10,386,399 B2
(45) Date of Patent: Aug. 20, 2019

(54) HUMAN BODY MODEL FOR WIRELESS SIGNAL MEASUREMENTS

(71) Applicant: BOSE CORPORATION, Framingham, MA (US)

(72) Inventor: Louis G. Chen, Bolton, MA (US)

(73) Assignee: BOSE CORPORATION, Framingham, MA (US)

( * ) Notice: Subject to any disclaimer, the term of this patent is extended or adjusted under 35 U.S.C. 154(b) by 130 days.

(21) Appl. No.: 15/679,001

(22) Filed: Aug. 16, 2017

(65) Prior Publication Data
US 2019/0056442 A1    Feb. 21, 2019

(51) Int. Cl.
| | | |
|---|---|---|
| *B32B 27/08* | (2006.01) | |
| *G01R 29/08* | (2006.01) | |
| *B32B 27/36* | (2006.01) | |
| *A61N 5/00* | (2006.01) | |
| *A61B 5/00* | (2006.01) | |
| *G09B 23/28* | (2006.01) | |

(52) U.S. Cl.
CPC ............ *G01R 29/0814* (2013.01); *A61B 5/00* (2013.01); *A61N 5/00* (2013.01); *B32B 27/08* (2013.01); *B32B 27/365* (2013.01); *G09B 23/28* (2013.01); *B32B 2307/204* (2013.01)

(58) Field of Classification Search
USPC ........................................................ 73/866.4
See application file for complete search history.

(56) References Cited

U.S. PATENT DOCUMENTS

| | | | | |
|---|---|---|---|---|
| 8,249,287 | B2* | 8/2012 | Silvestri | H04R 1/1016 381/380 |
| 9,866,946 | B2* | 1/2018 | Chen | H04B 1/385 |
| 2010/0015918 | A1* | 1/2010 | Liu | H04B 5/00 455/41.1 |
| 2011/0082523 | A1* | 4/2011 | Nghiem | A61N 1/37229 607/60 |

(Continued)

FOREIGN PATENT DOCUMENTS

| | | |
|---|---|---|
| DE | 2736380 A1 | 2/1979 |
| WO | 2016051206 A1 | 4/2016 |

OTHER PUBLICATIONS speag.com "TORSO phantom for Over the Air testing V5.1," https://www.speag.com/products/em-phantom/phantoms/torso-ota-v5-1/ [Accessed Online May 31, 2017].

(Continued)

*Primary Examiner* — Natalie Huls
*Assistant Examiner* — Mohammed E Keramet-Amircolai
(74) *Attorney, Agent, or Firm* — Patterson + Sheridan, LLP

(57) ABSTRACT

Aspects of the present disclosure provide an improved material structure for a human body model. The human body model comprises (1) a first layer comprising a first material, (2) a second layer, comprising a second material, underneath the first layer, and (3) a third layer, comprising a third material, underneath the second layer. The dielectric constant of the second material is less than a dielectric constant of the first material and less than a dielectric constant of the third material. According to an aspect, the thickness of the first and/or second layer may represent the thickness of human skin and fat, respectively. The thickness of one or more layers may vary based on a location on the human body model.

16 Claims, 5 Drawing Sheets

(56) References Cited

U.S. PATENT DOCUMENTS

| | | | |
|---|---|---|---|
| 2015/0045663 A1* | 2/2015 | Palikaras | A61B 5/0507 |
| | | | 600/430 |
| 2015/0268529 A1* | 9/2015 | Lin | G02F 1/163 |
| | | | 359/275 |
| 2015/0319531 A1* | 11/2015 | Kawka | H04R 1/00 |
| | | | 381/398 |
| 2016/0007110 A1* | 1/2016 | Silvestri | H04R 1/2849 |
| | | | 381/380 |

OTHER PUBLICATIONS

International Search Report and Written Opinion for International Application No. PCT/US2018/039481 dated Sep. 18, 2018, 13 pp.

* cited by examiner

HUMAN BODY MODEL FOR WIRELESS SIGNAL MEASUREMENTS

BACKGROUND

Aspects of the present disclosure generally relate to wireless technology and, more particularly, a material structure for a human body model.

Using live human participants for testing and validating wireless devices poses challenges, especially so for wearable devices due to the presence of human bodies as part of a boundary condition. It is difficult for humans to stand still for long periods of time, for the sake of maintaining the stationary boundary condition. Accordingly, human models (known as artificial human phantoms) that attempt to approximate the human body are used to validate design and/or performance of wireless devices. Additionally, human body models provide repeatability of measurements. In-view of the prevalence of wireless devices, a need exists for a more accurate human body model that may be used for wireless device design and performance validation.

SUMMARY

All examples and features motioned herein can be combined in any technically possible manner.

Certain aspects provide a material structure for a human body model, including (1) a first layer comprising a first material, (2) a second layer, comprising a second material, underneath the first layer, and (3) a third layer, comprising a third material, underneath the second layer. The dielectric constant of the second material is less than a dielectric constant of the first material and less than a dielectric constant of the third material.

According to an aspect, the dielectric constant of the first material approximates a dielectric property of human skin. According to an aspect, the dielectric constant of the first material approximates a dielectric property of dry human skin. According to an aspect, the dielectric constant of the second material approximates a dielectric property of human fat. According to an aspect, the dielectric constant of the third material approximates a dielectric property of human muscle. According to an aspect, the dielectric constant of the third material is greater than the dielectric constant of the first material.

According to an aspect, a thickness of the first layer approximates a thickness of human skin. According to one example, the thickness of the first layer of a portion of the human body model below the neck is greater than or equal to the thickness of the first layer of a portion of the human body model above the neck.

According to an aspect, a thickness of the second layer approximates a thickness of human fat. In one example, the thickness of the second layer of a portion of the human body model below the neck is greater than the thickness of the second layer of a portion of the human body model above the neck.

According to an aspect, a material structure for a human body model, includes a first layer approximating a dielectric property of human skin, a second layer approximating a dielectric property of human fat, and a third layer approximating a dielectric property of human muscle. In one example, the second layer is between the first and third layer.

According to an aspect, the second layer approximating the dielectric property of human fat includes a material having a dielectric constant less than a dielectric constant of a material comprising the first layer and less than a dielectric constant of a material comprising the third layer. According to an aspect, the dielectric constant of the third material is greater than the dielectric constant of the first material.

According to an aspect, the first layer approximates a thickness of human skin and the second layer approximates a thickness of human fat. According to an aspect, a thickness of the first layer of a portion of the human body model below the neck is greater than or equal to a thickness of the first layer of a portion of the human body model above the neck.

According to an aspect, a thickness of the second layer of a portion of the human body model below the neck is greater than a thickness of the second layer of a portion of the human body model above the neck. According to an aspect, the second layer comprises a polycarbonate material.

According to an aspect, a material structure for a human body model includes a first layer approximating a thickness and a dielectric property of human skin, a second layer approximating a thickness and a dielectric property of human fat, and a third layer approximating a dielectric property of human muscle. According to an aspect, the second layer is between the first layer and the third layer and wherein a dielectric constant of the second layer is less than a dielectric constant of the first layer and the dielectric constant of the first layer is less than a dielectric constant of the third layer.

According to an aspect, the thickness of at least one of the first layer or the second layer varies based on a location of the first layer or the second layer on the human body model.

According to an aspect, the dielectric property of human skin comprises a dielectric property of dry human skin.

Advantages of the material structure described herein include providing a more accurate proxy for the human body. The material structure may be used to simulate near field propagation effects on the human body. Other features and advantages will be apparent from the description and the claims.

DETAILED DESCRIPTION

Figure 1:
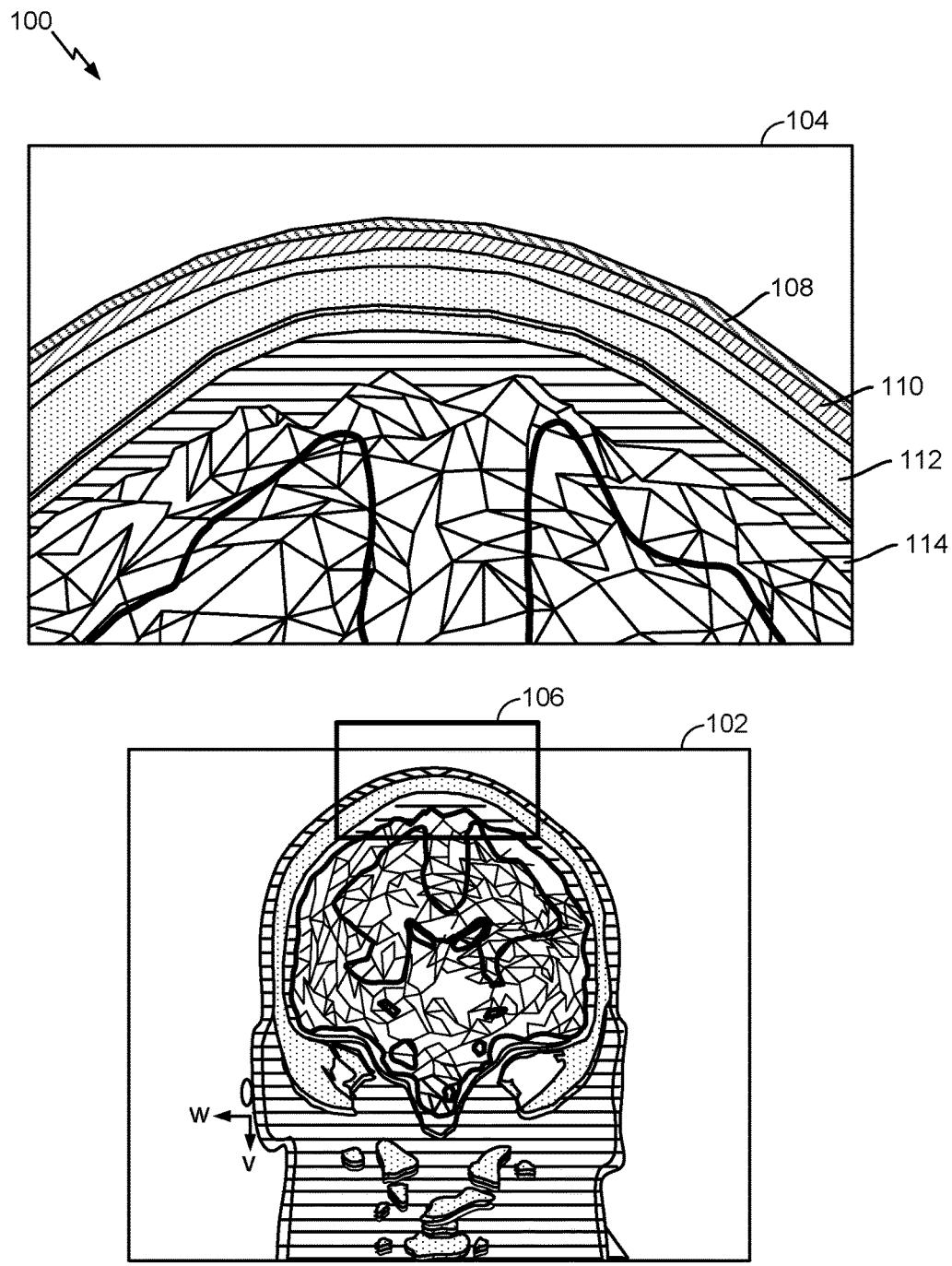
FIG. 1 illustrates an example cross-section of a portion of the human head.

Human body models are used for wireless device design verification across various industries. For example, human body models are used for design verification in the cell phone and hearing aid industries. As will be described in more detail with reference to Table 1, human tissue is characterized by having large dielectric constants. Therefore, electromagnetic propagation from a wireless device towards the human body is predominantly either absorbed or reflected away from the body.

For a wireless device having at least one antenna, the antenna radiation pattern may vary based its relative distance to the human body. For example, an antenna may be de-tuned due to loading from human tissue. For at least these reasons, cell phone antennas and hearing aids may be designed in an effort to maintain radiation performance with or without the presence of a human body.

Previously, human body models were used to test and validate wireless devices for far field radiation patterns, such as a user holding a cell phone that communicates with one or more cell towers, wherein at least one of the cell towers may be miles away from the cell phone. In addition to testing and validating far field radiation patterns, a human body model may be used to test near field applications. The need for a human body model that more closely approximates the human body may be seen with reference to wearable technology or smart electronic devices. In one example, a user may wear an audio device having an ear cup placed over an ear or an ear bud placed inside the ear. The audio device may wirelessly connect to another wireless device on (or close to) to the user's body via a wireless protocol. As an example, the audio device may include headphones. Example wireless protocols include Bluetooth, Bluetooth Low Energy (BLE), Near Field Communications (NFC), IEEE 802.11, or other local area network (LAN) or personal area network (PAN) protocols.

In one example, the audio device may communicate with the user's cell phone to play music or make a phone call. The signals exchanged between the audio device and the cell phone may interact intimately with the user's body. As an example, because the distance between the two wireless devices may be small, there may be little free space between the devices. Accordingly, the signals may propagate through or around the user's body. Given the use of wearable technology, more accurate human body models are needed to better represent the human body to validate designs for far field and near field applications.

Existing human body models use materials in an effort to mimic bio-tissues. According to an example, human body models are constructed using a plastic shell which encloses gel-like material. In an example, the gel-like material has a high dielectric constant.

Aspects of the present disclosure provide an improved structure for a human body model. According to an example, the structure is used to simulate the human body for wireless device design validation. As described herein, the material structure may include three layers: (1) a first layer comprising a first material, (2) a second layer, comprising a second material, underneath the first layer, and (3) a third layer, comprising a third material, underneath the second layer. According to an example, the dielectric constant of the first material approximates a dielectric property of human skin, the dielectric constant of the second material approximates a dielectric property of human fat, and the dielectric constant of the third material approximates a dielectric property of human muscle. As described herein, the dielectric constant of the second layer may be the less than the dielectric constant of the first layer, and the dielectric constant of the first layer may be less than the dielectric constant of the third layer. Thus, the dielectric constant of the second material is less than a dielectric constant of both the first material and a dielectric constant of the third material.

According to aspects, in an effort to more accurately model the human body, the thickness of the layers may vary based, at least in part, on location of the body. Human skin and underlying fat are generally thicker below the neck of a body. Accordingly, in one example, the first layer, which approximates skin, has a thickness below the neck of the human body model which is greater than or equal to a thickness of the first layer above the neck on the human body model. The thickness of the first layer above the neck is any value greater than 1 mm. Below the neck, the thickness of the first layer may be greater than or equal to the thickness above the neck. In one example, the thickness of the first layer is just slightly greater than 1 mm. According to another example, for illustrative purposes only, the thickness of the first layer may be approximately 2 to 3 mm above the neck and approximately 3 to 4 mm below the neck.

In an example, the second layer, which approximates human fat, has a thickness below the neck of the human body model which is greater than the thickness of the second layer above the neck. The thickness of the second layer above the neck is any value greater than 1 mm. In one example, the thickness of the second layer is just slightly greater than 1 mm. According to another example, for illustrative purposes only, the thickness of the second layer may be approximately 2 mm above the neck and approximately 4 mm below the neck.

In an effort to determine how electromagnetic propagation behaves around a human body, reflection and refraction of electromagnetic propagation from a wearable antenna can be analyzed. In one example, reflection and refraction is analyzed at each of the skin, fat, and muscle layers. Reflection and refraction of the electromagnetic signal impacts an antenna's far field radiation and surface diffracted grazing (creeping) effect. Analyzing the effect of electromagnetic waves on a human body requires a valid body model.

As noted above, currently-available human body models are typically composed of two layers including a shell and a gel material. The shell may be composed of a plastic or polycarbonate material having a low dielectric constant. The gel typically has a higher dielectric constant as compared to the dielectric constant of the shell. In reality, however, as illustrated in FIG. 1, the surface layers of human bio-tissue include, at least, skin, fat, and muscle. Thus, currently-available human body models are not representative of actual human body bio-tissue layers.

FIG. 1 illustrates an example cross-section 100 of a human head. At 102, a cross-section of the human head is illustrated. At 104, a zoomed-in version of a portion 106 of the human head 102 is illustrated. Skin is illustrated at 108. A layer of fat 110 is illustrated below the layer of skin 108. Muscle 112 is illustrated below the fat 110. The skull and grey matter 114 are illustrated below the layer of muscle 112. Each of the skin 108, fat 110, and muscle 112 may be associated with a dielectric constant value or a range of values.

When an electromagnetic plane wave is incident upon the surface, the dielectric constant of the first layer of a human body model pays a critical role. The higher the dielectric constant, the higher the reflection and the lower the refracted angle.

Table 1 provides example dielectric constants at 2.4 GHz for human skin, human fat, human muscle, an artificial shell of a human body model, and an artificial gel of the human body model. The dialectic constants provided in Table 1 are provided for illustrative purposes only. In Table 1, a lossy component of each of the materials includes a complex component i.

TABLE 1

| Material Type | Dielectric Constant at 2.4 GHz |
| --- | --- |
| Skin | 38.06 − 10.79*i |
| Fat | 5.28 − 0.77*i |
| Muscle | 52.79 − 12.77*i |
| Artificial Shell | 3.5 − 0.105*i |
| Artificial Gel | 39.2 − 9.48*i |

Figure 2:
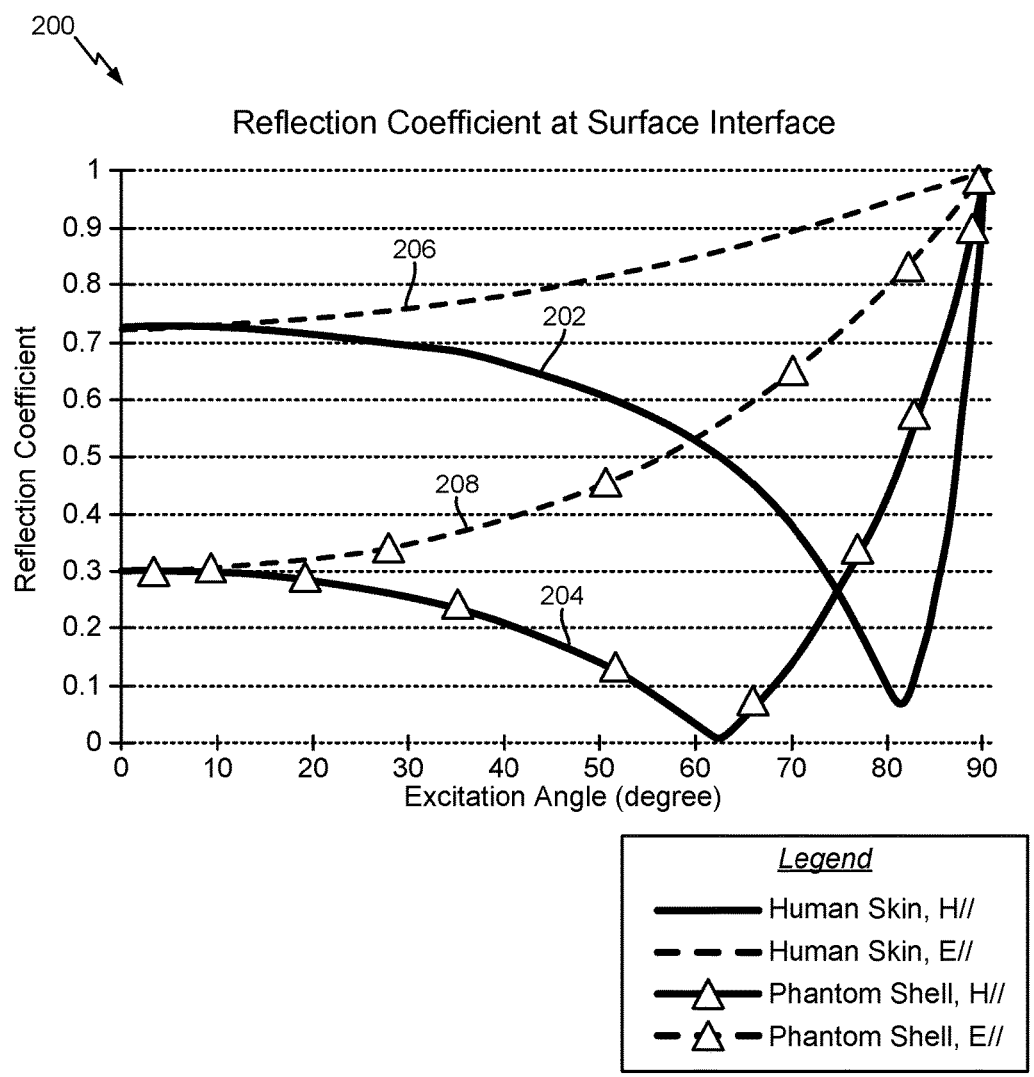
FIG. 2 illustrates an example plot of the reflection coefficient versus the excitation angle for human skin and a phantom shell, in accordance with aspects of the present disclosure.

FIG. 2 illustrates an example plot 200 of the reflection coefficient versus the excitation angle for human skin and a phantom shell representative of currently-available human body models. An arbitrarily polarized electromagnetic wave is a superposition of two polarized components: a magnetic field parallel to an interface and an electric field parallel to the interface. The magnetic field component is denoted as "H//" and the electric field component is denoted at "E//."

The plot 200 illustrates the magnetic field parallel to the skin at 202 and the magnetic field parallel to the phantom shell at 204. The plot 200 illustrates the electric field parallel to the skin at 206 and the electric field parallel to the phantom shell at 208.

As shown at 202 and 206, human skin has a higher reflection coefficient as compared to the phantom shell as shown at 204 and 208. Thus, the phantom shell representative of currently-available human body models allows more electromagnetic energy to penetrate the surface layer than human skin.

As seen in Table 1, the example dielectric constant of the artificial shell does not accurately represent the dielectric constant of human skin. According to aspects, a material having a high dielectric constant disposed on the top of the phantom shell would better mimic the surface reflection/refraction behavior of a human body. According to an example, a material having a dielectric constant greater than the dielectric constant of the artificial shell will more accurately approximate human skin. In one example, a material having a dielectric constant of approximately 24.4-7.32*i better approximates a reflection coefficient to human skin. More generally, the material structure described herein uses a material structure having an outer layer made of a material having a dielectric constant closer to 38.06-10.79*i (an example dielectric constant of human skin as provided in Table 1), which is different than the dielectric constant of existing phantom shells.

Figure 3:
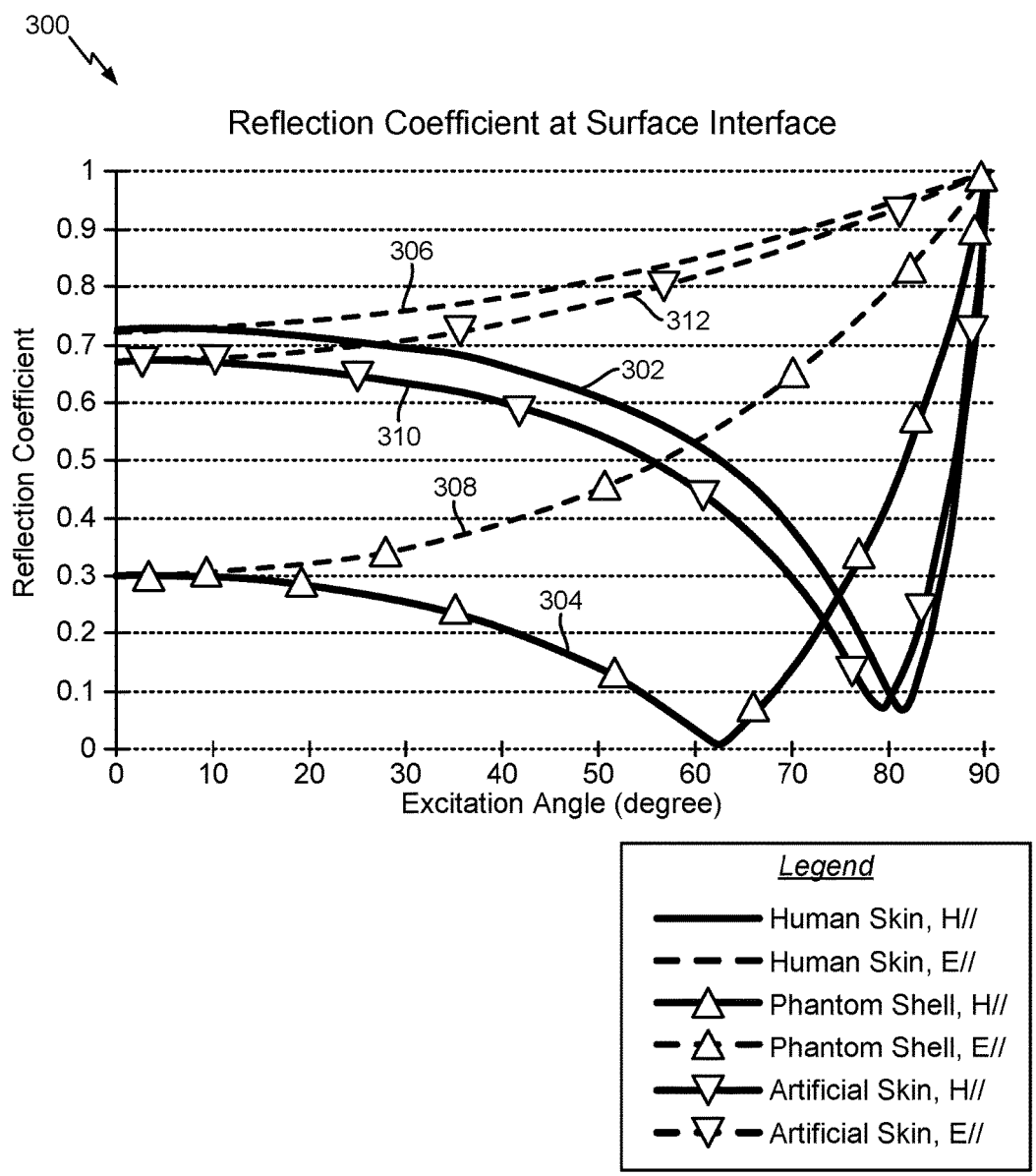
FIG. 3 illustrates an example plot of the reflection coefficient versus the excitation angle for human skin, a phantom shell, and artificial skin, in accordance with aspects of the present disclosure.

FIG. 3 illustrates an example plot 300 of the reflection coefficient versus the excitation angle for human skin, phantom shell, and artificial skin. In FIG. 2, the phantom shell was the outer layer of the human body model. In FIG. 3, instead of using the phantom shell as the outer layer of the human body model, an artificial skin made of a material having a dielectric constant closer to human skin is used as the outer layer. In one example, the dielectric constant of the artificial skin is greater than 3.5-0.105*i. The artificial skin used as the outer layer of the human body model in FIG. 3 has a dialectic constant that is approximately 24.4-7.32*i.

Similar to FIG. 2, the plot 300 illustrates the magnetic field parallel to the skin at 302 and the magnetic field parallel to the phantom shell at 304. The plot 300 illustrates the electric field parallel to the skin at 306 and the electric field parallel to the phantom shell at 308. Additionally, FIG. 3 illustrates the magnetic field parallel to artificial skin at 310 and the electric field parallel to artificial skin at 312.

As shown in FIG. 3, as compared to the phantom shell, the artificial skin more closely approximates the reflection coefficient of human skin. For example, the plot of the magnetic field parallel to the artificial skin at 310 more closely tracks plot 302. Similarly, the plot of the electric field parallel to the artificial skin at 312 more closely tracks the plot 306.

In FIGS. 2 and 3, a portion of an electromagnetic wave which contacted the outer layer of the human body model was reflected away and a portion penetrated by the outer layer. As described in FIG. 1, the human body has multiple layers, including skin, fat, and muscle. When an electromagnetic wave contacts the skin layer, a portion may be reflected away from the skin and a portion may penetrate the skin. The penetrating signals travel through the fat layer. Some of the penetrating signals will be reflected away at the muscle interface while other will penetrate the muscle. In an effort to mimic the many interactions that occur when an electromagnetic wave contacts the human body, a cascade of multiple material properties of the human body model may represent the propagation effect through a transmission coefficient. The transmission coefficient may be defined as (1−(reflection coefficient)^2)^0.5, assuming the loss at all interfaces and layers is negligible.

Figure 4:
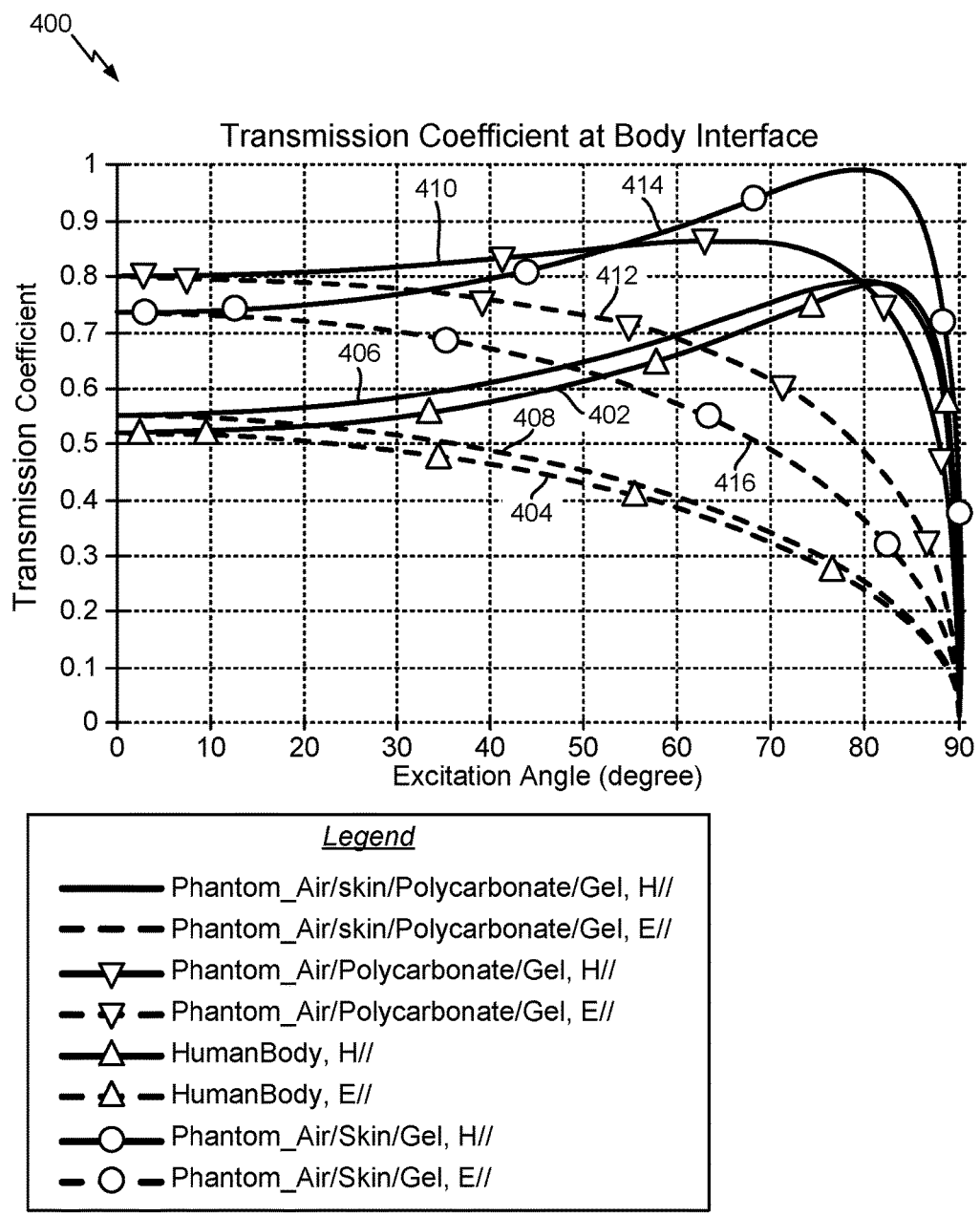
FIG. 4 illustrates an example plot of the transmission coefficient verses the excitation angle for several human body models, in accordance with aspects of the present disclosure.

FIG. 4 illustrates an example plot 400 of the transmission coefficient verses the excitation angle for several human body models. In FIG. 4, the transmission coefficient is illustrated for the human body and three human body models. The three human body models include (1) a model comprising an outer layer of artificial skin, a polycarbonate shell below the outer layer, and a gel material below the polycarbonate shell, (2) a model comprising an outer polycarbonate shell encasing a gel material, and (3) a model comprising an outer artificial skin layer above a gel material.

Plots 402 and 404 illustrate example magnetic and electric fields parallel to the human body, respectively. Plots 406 and 408 illustrate example magnetic and electric fields parallel to a model comprising an outer layer of artificial skin, a polycarbonate shell below the outer layer, and a gel material below the polycarbonate shell, respectively. Plots 410 and 412 illustrate example magnetic and electric fields parallel to a model comprising an outer polycarbonate shell encasing a gel material, respectively. Plots 414 and 416 illustrate example magnetic and electric fields parallel to a model comprising an outer artificial skin layer encasing a gel material, respectively.

As illustrated in FIG. 4, the plots 406 and 408 most closely approximate the example magnetic and electric fields parallel to the human body illustrated at 402 and 404, respectively. Thus, the total penetration of electromagnetic propagation of a human body model comprising an outer, artificial skin layer, a polycarbonate shell below the artificial skin layer, and a gel material below the polycarbonate shell resembles the human body. More transmission (or penetration) means the wavefronts of electromagnetic propagation across the material interfaces have a better continuity.

In addition to the artificial skin layer, the presence of a low dielectric material sandwiched between the artificial skin layer and the gel material also contributes to the overall reflection and transmission characteristics. As seen in FIG. 4, without the polycarbonate shell between the artificial skin and the gel, as seen at 414 and 416, the overall transmission (penetration) is higher than a human body model with a polycarbonate shell between the artificial skin layer and the gel layer, as shown at 406 and 408.

The three-layer material structure including an outer artificial skin layer, polycarbonate shell below the artificial skin layer, and gel material below the polycarbonate shell, may deviate from actual human tissues in terms of electrical properties; however as seen in FIG. 4, this material structure produces a better proxy for the human body compared to existing human body models.

An antenna of a wireless wearable device may be placed close to the surface of a human body model. In one example, nearly half of the radiation field is obstructed by the human body. If the body model generates less reflection from antenna excitation, the reflected waves would less likely perturb the radiation away from the body. A human body model with less reflection produces a stronger radiated power from the far field point of view and yields a stronger creeping effect from surface-grazing point of view.

Figure 5:
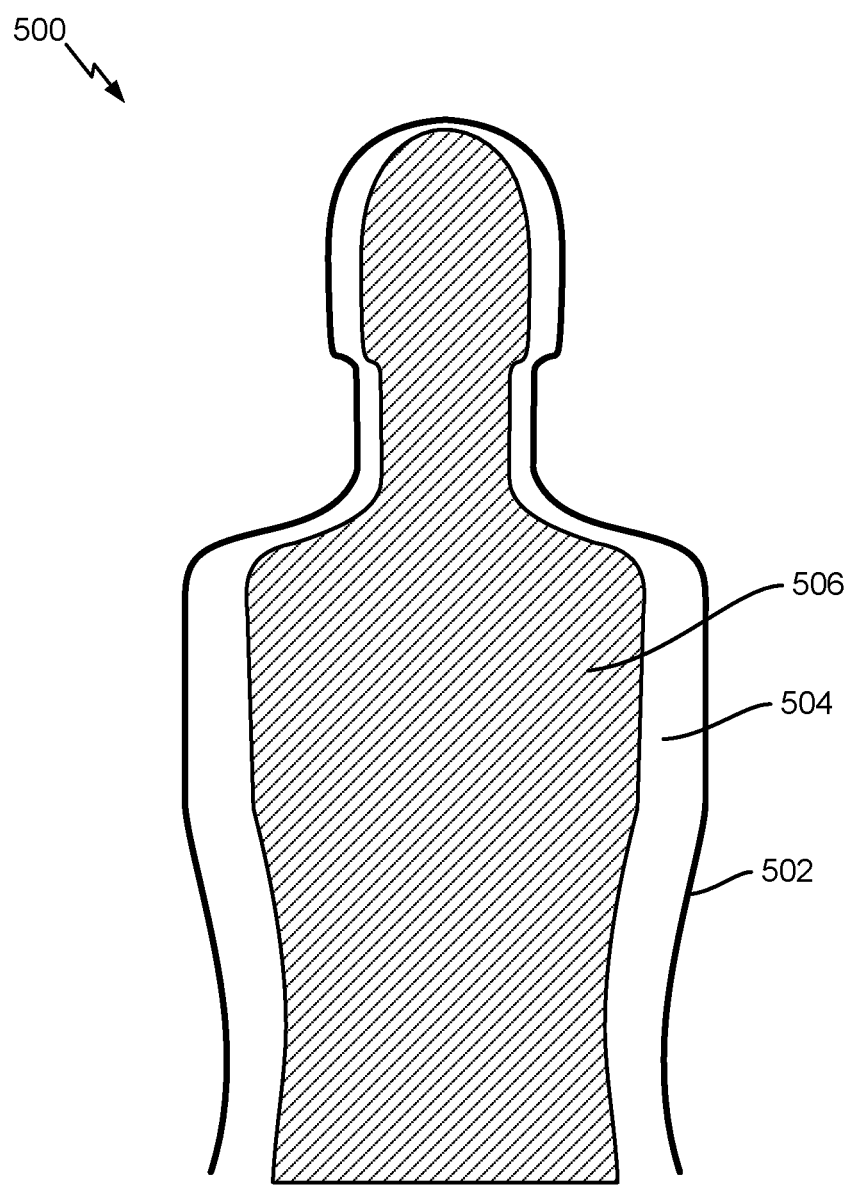
FIG. 5 illustrates an example human body model, in accordance with aspects of the present disclosure.

FIG. 5 illustrates an example human body model 500 in accordance with aspects of the present disclosure. The human body model is made up of a three-layer material structure. The first layer is made up of a material 502 that approximates a dielectric property of human skin. In one example, the first material approximates a property of dry human skin. In one example, the first layer 502 comprises a carbon loaded silicone. The second layer is made up of a material 504 that approximates a dielectric property of human fat. The third layer is made up of a material 506 that approximates a dielectric property of human muscle. The second layer 504 is between the first layer 502 and the third layer 506.

In addition to the three-layer structure described herein, according to aspects of the present disclosure, the thickness of one or more of the layers approximates a thickness of the tissue layer in the human body. In one example, the thickness of a layer may vary based, at least in part, on the location on the human body model. Skin and fat on a human body may be thicker below the neck as compared to above the neck. Accordingly, a thickness of a particular layer of the material structure described herein may depend on the location of the human body model.

For example, the outer, first layer 502 may be made of a material that is approximately 1 mm thick. In certain aspects, and as illustrated in FIG. 5, the first layer 502 is thicker below the neck of the human body model as compared to above the neck. For example, the first layer may be slightly greater than 1 mm above the neck and thicker below the neck. As another example, the first layer may be approximately 2 to 3 mm thick above the neck and 3 to 4 mm thick below the neck. Similarly, as illustrated in FIG. 5, the second layer 504 may be thicker below the neck of the human body model. The second layer 504 may be slightly greater than 1 mm above the neck and thicker below the neck. As another example, the second layer may be approximately 2 mm thick above the neck and may be thicker below the neck. In an example, the second layer may be approximately 4 mm thick below the neck.

Existing commercially-available human body models used as a human proxy in the laboratory make a wearable antenna perform better than it does in reality. By adding a material having a high dielectric constant disposed outside the polycarbonate shell, the human body model better mimics actual human bodies. Accordingly, an outer material having a high dialectal constant would enable a better correlation between simulated results laboratory measurements.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

The invention claimed is:

1. A material structure for a human body model, comprising:
   a first layer comprising a first material,
   a second layer, comprising a second material, underneath the first layer; and
   a third layer, comprising a third material, underneath the second layer,
   wherein a dielectric constant of the second material is less than a dielectric constant of the first material and less than a dielectric constant of the third material, and
   wherein the human body model comprises a neck, a thickness of the second layer approximates a thickness of human fat, and the thickness of the second layer of a portion of the human body model below the neck is greater than the thickness of the second layer of a portion of the human body model above the neck.

2. The material structure of claim 1, wherein the dielectric constant of the first material approximates a dielectric property of human skin.

3. The material structure of claim 1, wherein the dielectric constant of the first material approximates a dielectric property of dry human skin.

4. The material structure of claim 1, wherein the dielectric constant of the second material approximates a dielectric property of human fat.

5. The material structure of claim 1, wherein the dielectric constant of the third material approximates a dielectric property of human muscle.

6. The material structure of claim 1, wherein the dielectric constant of the third material is greater than the dielectric constant of the first material.

7. The material structure of claim 1, wherein a thickness of the first layer approximates a thickness of human skin.

8. The material structure of claim 7, wherein the thickness of the first layer of a portion of the human body model below the neck is greater than or equal to the thickness of the first layer of a portion of the human body model above the neck.

9. A material structure for a human body model, comprising:
   a first layer approximating a dielectric property of human skin,
   a second layer approximating a dielectric property of human fat; and
   a third layer approximating a dielectric property of human muscle,
   wherein the second layer is between the first and third layer,
   wherein the human body model comprises a neck, a thickness of the second layer approximates a thickness of human fat, and the thickness of the second layer of a portion of the human body model below the neck is greater than the thickness of the second layer of a portion of the human body model above the neck.

10. The material structure of claim 9, wherein the second layer approximating the dielectric property of human fat comprises:
    a material having a dielectric constant less than a dielectric constant of a material comprising the first layer and less than a dielectric constant of a material comprising the third layer.

11. The material structure of claim 10, wherein the dielectric constant of the third material is greater than the dielectric constant of the first material.

12. The material structure of claim 9, wherein the first layer approximates a thickness of human skin.

13. The material structure of claim 9, wherein a thickness of the first layer of a portion of the human body model below the neck is greater than or equal to a thickness of the first layer of a portion of the human body model above the neck.

14. The material structure of claim 9, wherein the second layer comprises a polycarbonate material.

15. A material structure for a human body model, comprising:
   a first layer approximating a thickness and a dielectric property of human skin,
   a second layer approximating a thickness and a dielectric property of human fat; and
   a third layer approximating a dielectric property of human muscle,
   wherein the second layer is between the first layer and the third layer and wherein a dielectric constant of the second layer is less than a dielectric constant of the first layer and the dielectric constant of the first layer is less than a dielectric constant of the third layer, and
   wherein the thickness of at least one of the first layer or the second layer varies based on a location of the first layer or the second layer on the human body model.

16. The material structure of claim 15, wherein the dielectric property of human skin comprises a dielectric property of dry human skin.

* * * * *